United States Patent [19]
Lindsay

[11] Patent Number: 5,713,909
[45] Date of Patent: Feb. 3, 1998

[54] VACUUM EXTRACTOR

[76] Inventor: Richard G. Lindsay, 6824 Elk Canyon Rd., Oklahoma City, Okla. 73162

[21] Appl. No.: 782,996

[22] Filed: Jan. 14, 1997

[51] Int. Cl.⁶ .................................................. A61B 17/42
[52] U.S. Cl. ........................... 606/123; 606/122; 604/149
[58] Field of Search ............................ 606/123, 121, 606/122, 124, 115; 604/97, 284, 147, 149

[56] References Cited

U.S. PATENT DOCUMENTS

| | | | |
|---|---|---|---|
| 667,447 | 2/1901 | Miller . | |
| 1,058,330 | 4/1913 | Page et al. | 604/149 |
| 1,071,931 | 9/1913 | Long | 604/149 |
| 2,702,038 | 2/1955 | Uddenberg et al. | 606/123 |
| 3,202,152 | 8/1965 | Wood et al. | 128/361 |
| 5,019,086 | 5/1991 | Neward | 606/123 |
| 5,163,944 | 11/1992 | Neward | 606/123 |
| 5,281,229 | 1/1994 | Neward | 606/123 |

OTHER PUBLICATIONS

"Soft-cup vacuum extractors safety assist normal deliveries," Frank R. Witter, MD, *Contemporary OB/GYN*, not dated, pp. 3–8.

"Instrumental delivery in the 1990s: a commentary," David Acker, MD, *Contemporary OB/GYN*, ©1985 and 1990, pp. 9–10.

*Primary Examiner*—Michael Buiz
*Assistant Examiner*—Julian W. Woo
*Attorney, Agent, or Firm*—Dunlap & Codding, P.C.

[57] ABSTRACT

A vacuum extractor for extracting a fetus from a birth canal during childbirth is provided. The vacuum extractor includes a cup, a stem, and a handle. The handle has a first end, a second end, and a passageway extending therethrough from the first end to the second end. The handle is connected to the stem such that the first and second ends of the handle extend substantially laterally from the stem and the passageway of the handle in fluid communication with the vacuum cup. The first end of the handle is adapted to be connected to a vacuum source, and the second end is adapted to receive a vacuum release valve.

7 Claims, 3 Drawing Sheets

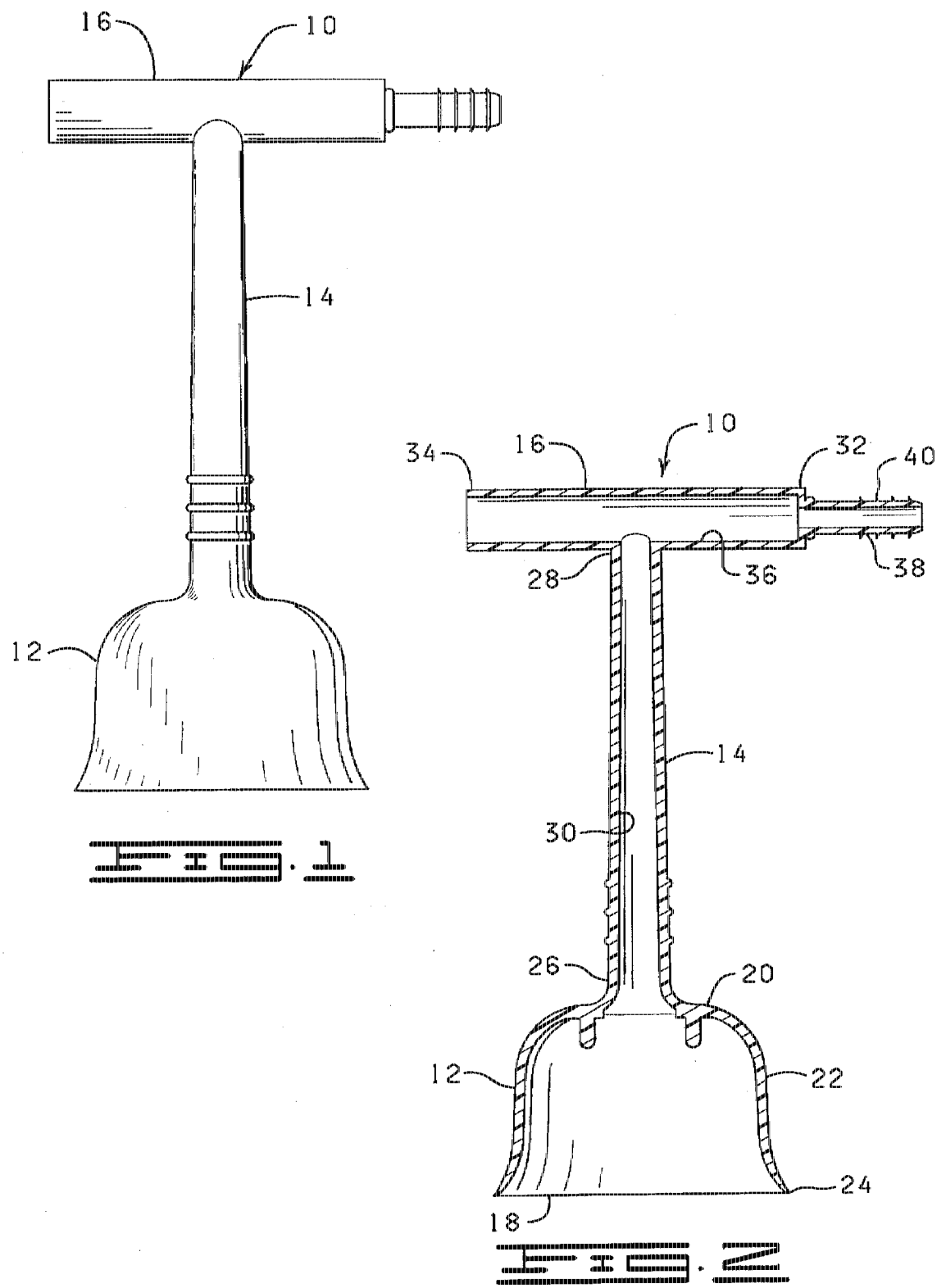

VACUUM EXTRACTOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates generally to obstetric extraction devices, and more particularly, but not by way of limitation, to an improved vacuum extractor having a laterally extending handle with a vacuum hose connection on one end thereof and a vacuum release valve connection on an opposing end thereof.

2. Description of Related Art

Many devices are known for assisting a physician in the extraction of a fetus from the birth canal during childbirth. Some of the devices include forceps and vacuum extractors. While each of these types of devices have been used successfully in the childbirthing process, problems in the use of each of these types of devices have nevertheless been experienced.

For example, the use of forceps has been known to cause severe injuries, in particular head injuries, to new born children. Also, due to the awkward shape of forceps, their use can cause discomfort and result in possible injury to the mother. In an effort to overcome the inherent problems associated with the use of forceps, vacuum extraction devices have been employed.

Vacuum extractors utilize a cup, the opening of which is applied to the fetal head after the device has been introduced into the birth canal. The cup is attached to a vacuum source to create a vacuum in the cup and thus adhere the cup to the fetal head. With the vacuum extractor adhered to the fetal head, the fetus can then be pulled from the birth canal by manipulating a handle provided on the end of the vacuum extractor.

A problem experienced with the use of vacuum extractors is their susceptibility to release from or "pop off" the fetal head. When a vacuum extractor repeatedly releases from a fetal head, the delivery time is increased and the opportunity for the infliction of fetal scalp abrasions is increased.

Periodically, a vacuum extractor releases from a fetal head as a result of erroneous technique when employing the vacuum extractor. Thus, a number of the "pop offs" that occur can be reduced by simply using proper technique. However, many "pop offs" result from a loss of vacuum pressure to the vacuum extractor due to an interruption of the vacuum to the vacuum extractor. This is due in large part to the fact that the prior art vacuum extractors are adapted to be connected to a vacuum source via a vacuum hose that is attached to the vacuum extractor at a point above the handle of the vacuum extractor along the longitudinal axis of the stem. In this location, the end of the vacuum hose is caused to be positioned in the palm of a physician's hand when the physician grips the handle of the vacuum extractor. As a consequence, the ability of the physician to comfortably grasp the vacuum extractor is interfered with, and more significantly, the potential exists for the vacuum hose to be bent or crimped by the physician's hand, thereby causing the vacuum pressure to the vacuum extractor to be inadvertently interrupted.

Also, for safety purposes, it is desirable when employing a vacuum extractor with certain types of vacuum units that the physician have the ability to immediately reduce or release the vacuum formed in the vacuum extractor. In an attempt to provide this ability, a vacuum release valve has been interposed between the vacuum extractor and the vacuum hose. However, due to the problem with the configuration of the prior art vacuum extractors discussed above, the release valve is caused to be located in the palm of a physician's hand when the physician grips the handle of the vacuum extractor, and thus is difficult for a physician to operate in an efficient manner.

To this end, a need has long existed for an improved vacuum extractor having a laterally extending handle with a passageway which is adapted to receive a vacuum hose so that the handle of the vacuum extractor can be grasped without interfering with the vacuum hose and which is adapted to receive a vacuum release valve wherein the vacuum release valve is efficiently and conveniently located on the vacuum extractor. It is to such an improved vacuum extractor that the present invention is directed.

BRIEF SUMMARY OF THE INVENTION

The present invention is directed to a vacuum extractor for extracting a fetus from a birth canal during childbirth. The vacuum extractor includes a cup, a stem, and a handle. The handle has a first end, a second end, and a passageway extending therethrough from the first end to the second end. The handle is connected to the stem such that the first and second ends of the handle extend substantially laterally from the stem and the passageway of the handle is in fluid communication with the vacuum cup. The first end of the handle is adapted to be connected to a vacuum source, and the second end is adapted to receive a vacuum release valve.

The objects, features and advantages of the present invention will become apparent from the following detailed description when read in conjunction with the accompanying drawings and appended claims.

BRIEF DESCRIPTION OF THE SEVERAL VIEWS OF THE DRAWING

FIG. 1 is an elevational view of a vacuum extractor constructed in accordance with the present invention.

FIG. 2 is a cross sectional view of the vacuum extractor of FIG. 1.

DETAILED DESCRIPTION OF THE INVENTION

Figure 3A:
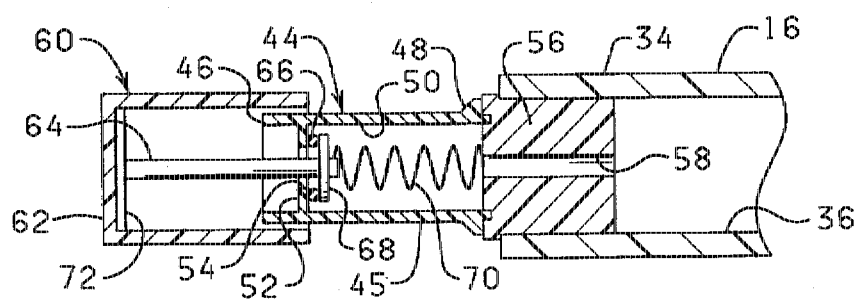
FIG. 3A is an enlarged cross sectional view of the second end of the handle shown with a vacuum release valve connected thereto and in a closed position.

Referring now to the drawings, and more particularly to FIGS. 1 and 2, a vacuum extractor 10 constructed in accordance with the present invention is illustrated. The vacuum extractor 10 includes a cup 12, a tubular stem 14, and a tubular handle 16. The vacuum extractor 10 is integrally formed from a suitable polymeric material, such as a virgin polyethylene, and by any suitable process, such as a conventional injection mold process which is well known to those of ordinary skill in the art.

The cup 12 is characterized as having an open bottom end 18, a top end 20, and a sidewall 22. The cup 12 is shown to be substantially bell-shaped and as having a thin flexible outer edge 24 to facilitate the formation of a seal between the cup 12 and a fetal head. However, it will be appreciated by those of ordinary skill in the art that the cup 12 may be formed into a variety of configurations so long as the outer edge of the cup and a fetal head are able to conform with one another so that a seal may be formed in the cup to adhere the cup to the fetal head.

The stem 14 is elongated and has a first end 26, a second end 28, and a passageway 30 extending therethrough from the first end 26 to the second end 28. The first end 26 of the stem 14 is connected to the top end 20 of the cup 12 such that the passageway 30 of the stem 14 is in fluid communication with the open bottom end 18 of the cup 12.

Similar to the stem 14, the handle 16 has a first end 32, a diametrically opposed second end 34, and a passageway 36 extending therethrough from the first end 32 to the second end 34. The handle 16 is connected to the second end 28 of the stem 14 with the first end 32 and the second end 34 of the handle 16 extending laterally from the second end 28 of the stem 14 whereby the handle 16 and the stem 14 are arranged in a substantially T-shaped configuration. The handle 16 is further connected to the second end 28 of the stem 14 such that the passageway 36 of the handle 16 is in fluid communication with the passageway 30 of the stem 14, and thus, the passageway 36 of the handle 16 and the passageway 30 of the stem 14 are arranged in a substantially T-shaped configuration.

Figure 4:
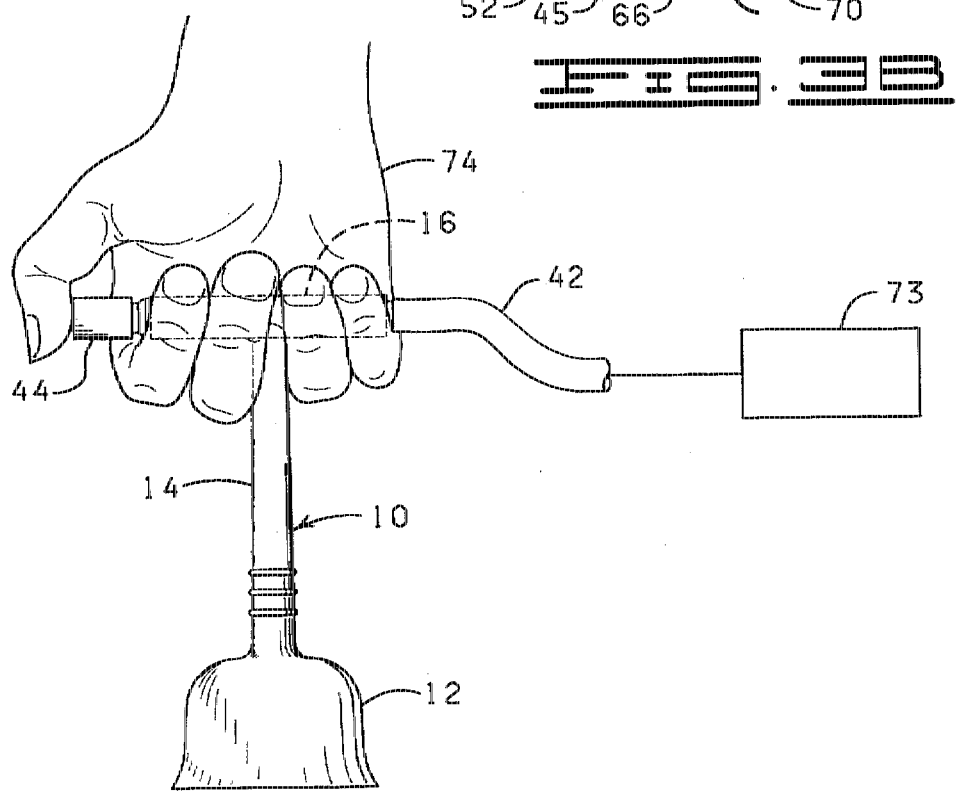
FIG. 4 is an elevational view of the vacuum extractor of the present invention illustrating the vacuum release valve connected to one end of the handle, a vacuum hose connected to the other end of the handle, and an individual gripping the handle.

The first end 32 of the handle 16 is configured to have a narrowed hose connector 38 which has a plurality of retaining ribs 40 for facilitating the connection of a vacuum hose 42 to the vacuum extractor 10, as illustrated in FIG. 4. The second end 34 of the handle 16 is adapted to receive a vacuum release valve as will be discussed in detail below. It will be appreciated, however, that the shape and size of both the first and second ends of the handle can be varied to receive a variety of different types of vacuum hoses and valves.

Figure 3B:
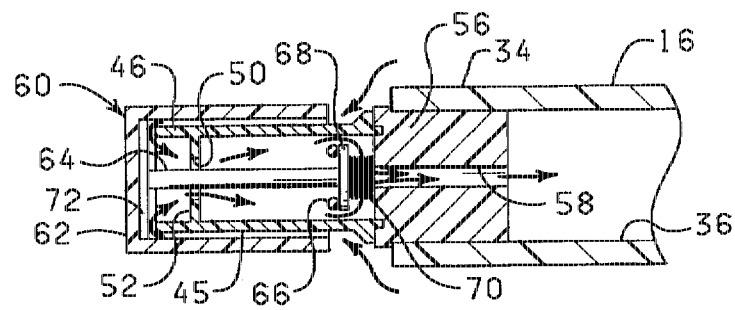
FIG. 3B is an enlarged cross sectional view of the second end of the handle shown with the vacuum release valve connected thereto and in an open position.

When it is necessary that a user of the vacuum extractor 10 be able to quickly release the vacuum formed in the vacuum extractor 10, a vacuum release valve 44 is connected to the second end 34 of the handle 16. A suitable valve is illustrated in FIGS. 3A and 3B. The valve 44 includes a valve body 45 having a first end 46, a second end 48, and a passageway 50 extending therethrough from the first end 46 to the second end 48. The valve body 45 further has an interior shoulder 52 with a central opening 54.

The first end 46 of the valve body 45 is connected to a handle adaptor member 56 which is shaped to be received in the second end 34 of the handle 16, as substantially shown in FIGS. 3A and 3B. It will be appreciated, however, that the handle adaptor member 56 can also be shaped to fit over the second end 34 of the handle 16 as opposed to fitting within the second end 34 of the handle 16. The handle adaptor member 56 has a centrally disposed flow passage 58 extending therethrough so as to establish fluid communication between the passageway 36 of the handle 16 and the passageway 50 of the valve body 45 when the valve 44 is connected to the second end 34 of the handle 16. The valve body 45 is connected to the handle adaptor member 56 by any suitable fashion, such as by sonic welding.

To selectively seal the central opening 54 of the valve body 45 from the passage 58 of the handle adaptor member 56, a push button assembly 60 is provided. The push button assembly 60 includes a button 62, a shaft 64, and a seal ring 66. The shaft 64 is provided with a flange 68 for supporting the seal ring 66 on one side thereof and for engaging a spring 70 on the opposite side thereof. The shaft 64 is disposed through the central opening 54 of the valve body 45 with the seal ring 66 positioned between the interior shoulder 52 and the flange 68 of the shaft 64. The distal end of the shaft 64 is connected to a central portion of the button 62, which is configured to extend over the second end 48 of the valve body 45.

The spring 70 is disposed between the handle adaptor member 56 and the flange 68 of the shaft 64 such that one end of the spring 70 engages the handle adaptor member 56 and the other end of the spring 70 engages the flange 68 of the shaft 64. In a closed position, illustrated in FIG. 3A, the spring 70 biases the flange 68 toward the interior shoulder 52 of the valve body 45 so as to cause the seal ring 66 to form a seal between the interior shoulder 52 and the flange 68. In an open position, illustrated in FIG. 3B, the flange 68 is forced away from the interior shoulder 52 by pushing on the button 62 thereby breaking the seal between the interior shoulder 52 and the flange 68. In the open position, air is able to flow through the flow passage 58 of the handle adaptor member 56, through the central opening 54 of the valve body 45, and between the second end 48 of the valve body 45 and the button 62, thereby releasing a vacuum formed in the cup 12.

To prevent the button 62 from forming a seal with the second end 48 of the valve body 45 when the button 62 is pushed, the button 62 is provided with a support rib 72. The rib 72 extends downwardly from the bottom side of the button 62 so as to engage the second end 48 of the valve body 45 when the button 62 is pushed thereby maintaining a flow path between the second end 48 of the valve body 45 and the button 62 when the release valve 44 is in the open position.

As mentioned above, FIG. 4 illustrates the vacuum extractor 10 with the vacuum hose 42 attached to the first end 32 of the handle 16. The vacuum hose 42 is diagrammatically illustrated as being connected to a vacuum source 73. FIG. 4 further illustrates the vacuum release valve 44 connected to the second end 34 of the handle 16 and an individual's hand 74 operably gripping the handle 16. It will be appreciated that the unique configuration of the handle 16 provides the advantage of enabling an individual to grip the handle 16 of the vacuum extractor 10 during delivery without being concerned about inadvertently interrupting the vacuum in the cup 12 by pinching or crimping the vacuum hose 42 in the palm of their hand. The unique configuration provides the further advantage of allowing the vacuum release valve 44 to be efficiently located so that the individual can quickly and easily operate the vacuum release valve 44 with their thumb without having to vary their grip of the handle 16.

Figure 5:
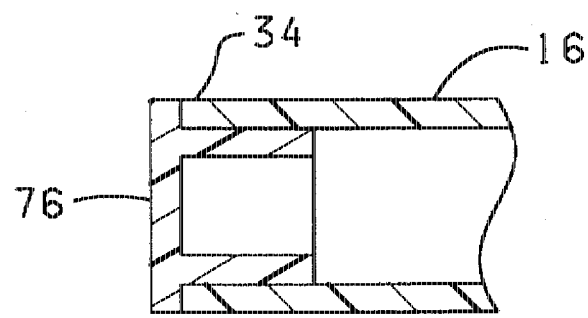
FIG. 5 is an enlarged cross sectional view of the second end of the handle with a plug disposed therein.

If the vacuum source to which the vacuum extractor 10 is being connected has a vacuum release, it may not be necessary to employ the valve 44. In those instances, the second end 34 of the handle 16 may be sealed with a plug 76, as illustrated in FIG. 5. The plug 76 is preferably dimensioned so that it may be press fitted in the second end 34 of the handle 16 and thus selectively removed therefrom. Alternatively, the plug 76 may be removably secured in the second end 34 of handle 16 with a suitable adhesive.

Figure 6:
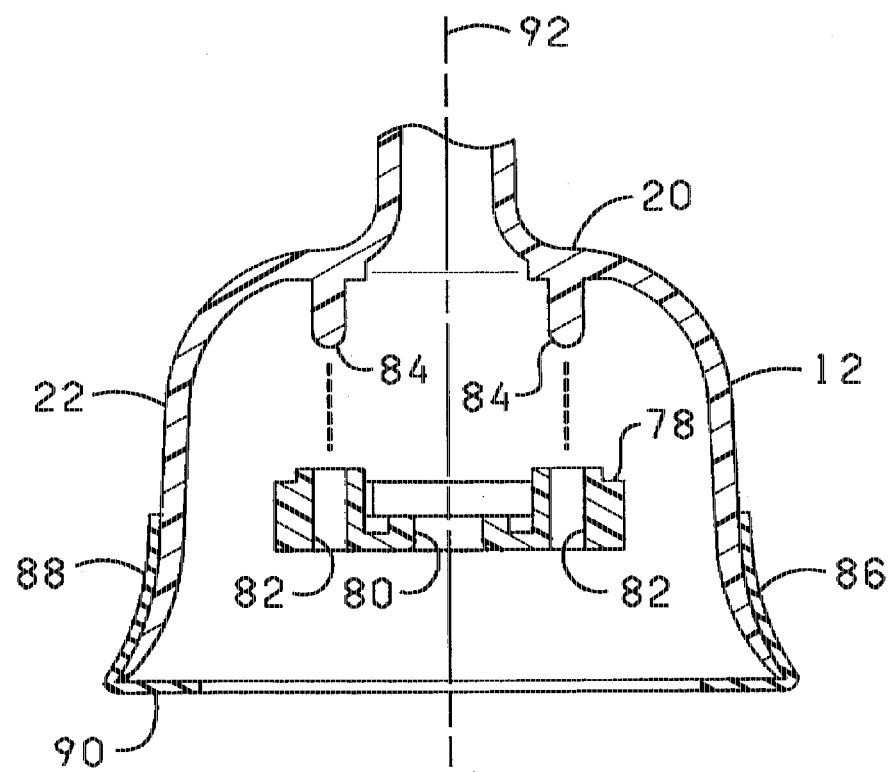
FIG. 6 is an enlarged cross sectional view of the cup illustrating a distributor disc and a protective sleeve.

Referring now to FIG. 6, a distributor disk 78 is provided in the cup 12 near the top end 20 thereof to limit the extent that the scalp of an infant may be drawn into the cup 12. The distributor disk 78 has a central opening 80 and a pair of openings 82. The openings 82 are sized to receive a pair of pegs 84 extending from the top end 20 of the cup 12. The distributor disk 78 is disposed on the pegs 84 such that the disk 78 is positioned in a spaced apart relationship relative to the top end 20 of the cup 12 and such that the outer edge of the disk 78 is spaced from the sidewall 22 of the cup 12 thereby providing a flow path around the disk 78. The disk 78 is secured to the pegs 84 by any suitable means, such as sonic welding.

To prevent the thin outer edge 24 of the cup 12 from cutting into the scalp of a fetus, a protective sleeve 86 can be positioned over the outer edge 24. The sleeve 86 has a first end portion 88 that is disposable about a lower portion of the sidewall 22 of the cup 12 and a second end portion 90 that is extendable radially inward over a portion of the bottom end 18 of the cup 12 in a substantially perpendicular relationship to a longitudinal axis 92 (FIG. 6) of the cup 12. The sleeve 86 is preferably formed from a soft, elastic material, such as rubber, so that the first end portion 88 of the sleeve 86 frictionally engages the sidewall 22 and the outer edge 24 of the cup 12 to retain the sleeve 86 on the cup 12 when the first end portion 88 of the sleeve 86 is disposed about the lower portion of the cup 12.

One of the advantages of using the sleeve 86 to cover the outer edge 24 of the cup 12, besides covering the outer edge 24 of the cup 12 with a soft, flexible layer of material, is that the sleeve 86 is positioned on the cup 12 such that the upper portion of the cup 12 is not covered. Thus, due to the translucent characteristics of virgin polyethylene, a physician is able to visually monitor how far into the cup 12 the fetal head has been drawn through the upper portion of the cup 12. Another notable advantage of the sleeve 86 is that by allowing the second end portion 90 of the sleeve 86 to extend radially inward over the open bottom end 18 of the cup 12, the second end portion 90 of the sleeve 86 is able to conform to the fetal head thereby providing a greater surface area with which the fetal head is in contact and aiding in preventing the cup 12 from sliding and rotating on the fetal head as a physician manipulates the vacuum extractor 10 during the delivery process.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed:

1. A vacuum extractor for extracting a fetus from a birth canal during childbirth, the vacuum extractor comprising:

a cup having an open bottom end, a top end, and a sidewall;

a substantially rigid stem having a first end, a second end, and a passageway extending therethrough from the first end to the second end, the first end of the stem connected to the top end of the cup such that the passageway of the stem is in fluid communication with the open bottom end of the cup; and a handle connected to the second end of the stem for facilitating manipulation of the stem and the cup to extract the fetus from the birth canal, the handle having a first end, a second end, and a passageway extending from the first end toward the second end, the first end of the handle extending substantially laterally from the second end of the stem and the passageway of the handle being in fluid communication with the passageway of the stem, the first end of the handle adapted to be connected to a vacuum source.

2. The vacuum extractor of claim 1 wherein the second end of the handle extends substantially laterally from the stem, wherein the passageway of the handle extends from the first end to the second end thereof, and wherein the vacuum extractor further comprises:

valve means connected to the second end of the handle for selectively releasing a vacuum formed in the cup.

3. The vacuum extractor of claim 2 wherein the first end of the handle is diametrically opposed from the second end of the handle.

4. The vacuum extractor of claim 1 wherein the cup is characterized as having a longitudinal axis and wherein the apparatus further comprises:

a protective sleeve having a first end portion and a second end portion, the first end portion of the sleeve disposed about a lower portion of the sidewall of the cup and the second end portion of the sleeve extending radially inward over a portion of the bottom end of the cup in a substantially perpendicular relationship to the longitudinal axis of the cup.

5. A vacuum extractor for extracting a fetus from a birth canal during childbirth, the vacuum extractor comprising:

a cup having an open bottom end, a top end, and a sidewall;

a substantially rigid stem having a first end, a second end, and a passageway extending therethrough from the first end to the second end, the first end of the stem connected to the top end of the cup such that the passageway of the stem is in fluid communication with the open bottom end of the cup;

a handle connected to the second end of the stem for facilitating manipulation of the stem and the cup to extract the fetus from the birth canal, the handle having a first end, a second end, and a passageway extending therethrough from the first end to the second end, the first and second ends of the handle extending laterally from the second end of the stem and the passageway of the handle being in fluid communication with the passageway of the stem, the first end of the handle adapted to be connected to a vacuum source; and a vacuum release valve connected to the second end of the handle for selectively releasing a vacuum formed in the cup.

6. The vacuum extractor of claim 5 wherein the first end of the handle is diametrically opposed from the second end of the handle.

7. The vacuum extractor of claim 5 wherein the cup is characterized as having a longitudinal axis and wherein the apparatus further comprises:

a protective sleeve having a first end portion and a second end portion, the first end portion of the sleeve disposed about a lower portion of the sidewall of the cup and the second end portion of the sleeve extending radially inward over a portion of the bottom end of the cup in a substantially perpendicular relationship to the longitudinal axis of the cup.

* * * * *